United States Patent
Jenkins et al.

(10) Patent No.: US 6,216,036 B1
(45) Date of Patent: Apr. 10, 2001

(54) IMPLANTABLE CARDIOVERTER DEFIBRILLATOR AND SYSTEM FOR TESTING SAME

(76) Inventors: Janice M. Jenkins, 13 Eastbury, Ann Arbor, MI (US) 48105-1402; Richard Jenkins, 230 E. Ontario #1105, Chicago, IL (US) 60610

( * ) Notice: Subject to any disclaimer, the term of this patent is extended or adjusted under 35 U.S.C. 154(b) by 0 days.

(21) Appl. No.: 09/252,043

(22) Filed: Feb. 17, 1999

Related U.S. Application Data

(60) Provisional application No. 60/074,907, filed on Feb. 17, 1998.

(51) Int. Cl.[7] .................................................. A61N 1/37
(52) U.S. Cl. ................................................................ 607/27
(58) Field of Search .................................... 607/27, 28, 5

(56) References Cited

U.S. PATENT DOCUMENTS

| | | | |
|---|---|---|---|
| 3,768,487 | * 10/1973 | Rose | 607/27 |
| 4,290,430 | * 9/1981 | Bihn et al. | 607/27 |
| 4,640,285 | * 2/1987 | DeCote, Jr. et al. | 607/27 |
| 4,705,042 | * 11/1987 | Giurtino | 607/27 |

\* cited by examiner

*Primary Examiner*—William E. Kamm
(74) *Attorney, Agent, or Firm*—Harness, Dickey & Pierce, P.L.C.

(57) ABSTRACT

An in-vitro testing system to assist in optimal programming of an ICD is provided which avoids the inconvenience and health risk associated with repetitive inductions of an arrhythmia. The system includes a high speed computer having analog-to-digital and digital-to-analog subsystems. The system includes software which provides real-time capture and storage of a patient's electrogram. Subsequently, the electrogram may be played and replayed into ICD software simulators at a variety of settings to determine candidate programming parameters. The system further includes an attenuator through which signals are fed on their way to an ICD. This arrangement provides a method by which validation of the simulation system may be achieved. The system also provides for the capture of output event markers simultaneously with the signal into a digital file for assessment of device performance.

5 Claims, 1 Drawing Sheet

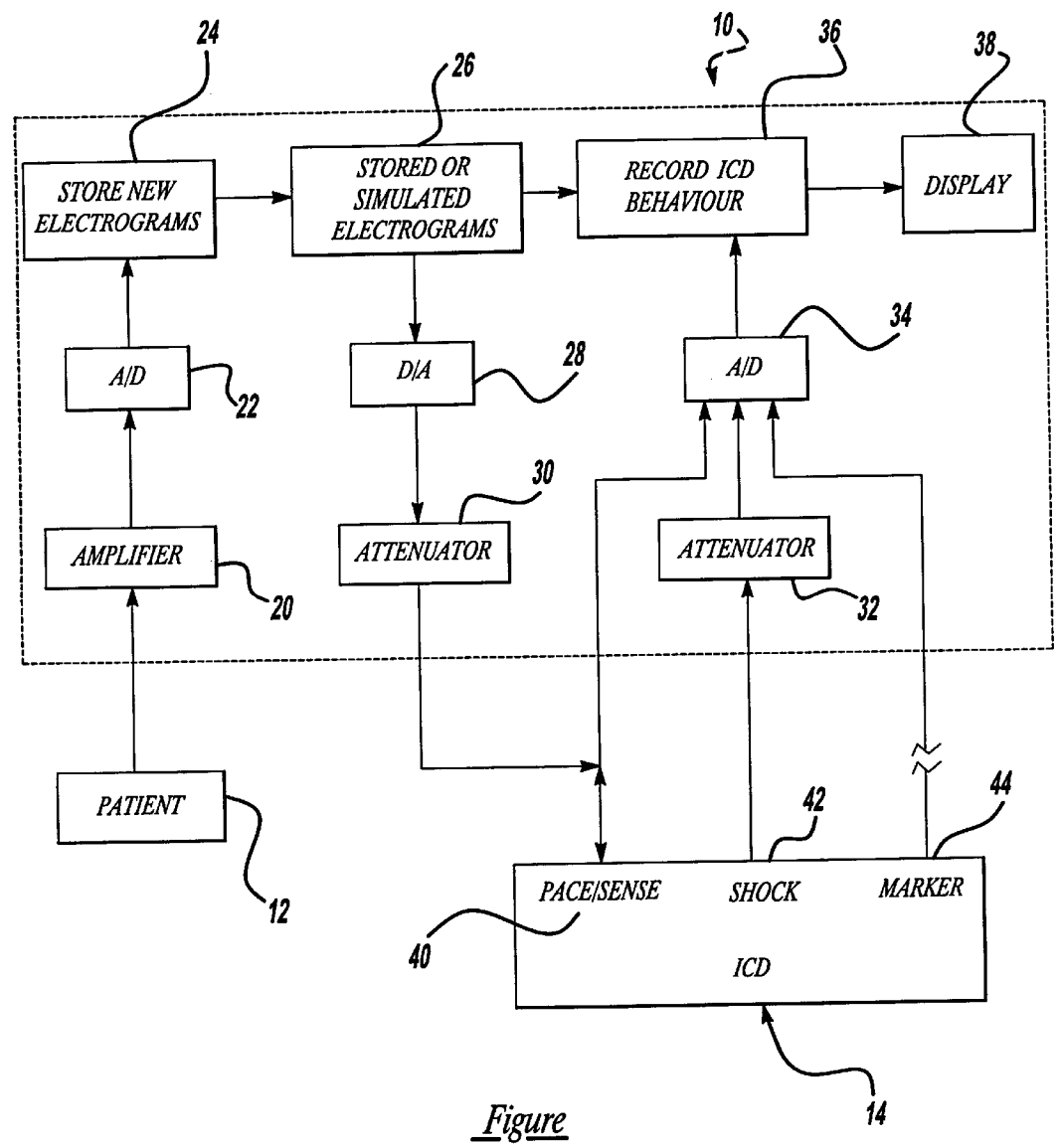
Figure

IMPLANTABLE CARDIOVERTER DEFIBRILLATOR AND SYSTEM FOR TESTING SAME

Priority based on U.S. Provisional Application No. 60/074,907, filed Feb. 17, 1998, is claimed under 35 U.S.C. 119(e).

BACKGROUND OF THE INVENTION

1. Technical Field

The present invention relates generally to a testing system for use in programming an implantable cardioverter defibrillator prior to implantation. More hardware and software designed to eliminate repeated arrhythmia induction by the real-time capture and storage of an electrogram which can be replayed into ICD software simulators to determine ICD programming parameters.

2. Summary of Related Art

The pumping action of the heart is effected by the spontaneous generation of an electrical impulse or action potential. The electrical impulse is conducted throughout the heart, causing subsequent contraction of the myocardium in response. The origin of the heart's electrical impulse is the sino-atrial node. The impulse is conducted to all portions of the atria through cell-to-cell transmission, whereby contraction of the atrial chambers results. Once initiated, the impulse continues to the atrioventricular node (or "A-V node"), which is a cluster of conduction fibrils. The A-V node functions as a delaying mechanism or a buffer to slow conductio of the received electrical impulse by about one-tenth of a second. This brief delay of transmission of electrical impulse from the atria to the ventricles allows for proper blood flow between the chambers.

The A-V node thereafter transmits an electrical impulse to the bundle of His. This bundle comprises the left and right bundle branches of the His-Purkinjie system. Purkinjie fibers are located at the terminal ends of the bundle branches, forming the electrical link to the myocardial cells themselves.

The conducted electrical impulses define a coordinated wave of electrical activity which effect simultaneous contraction of plural myocardial cells. The impulses initially cause depolarization, and sequential contraction of cardiac muscle of the atria and ventricles follows.

While the electrical system of the heart operates with astonishing regularity in most people, proper functioning is impaired when the heart experiences aberrations in electrical origination or transmission. When electrical failure or a change from normal electrical transmission occurs, the result is a change in sequence of cardiac activity or an arrhythmia. An arrhythmia may be atrial, atrioventricular, or ventricular. Ventricular tachycardia and ventricular fibrillation are of greatest concern and may be lethal. During an episode of ventricular tachycardia, the sequence of ventricular extrasystoles occurs at a rate of between 110 and 240 cycles per minute. If sustained, ventricular tachycardia may eventually lead to ventricular fibrillation in which the ventricular extrasystoles reach a frequency in excess of 330 cycles per minute. It is the sustained ventricular tachycardia which may lead to death if not resolved within minutes.

There are a variety of approaches to the treatment of arrhythmia. Approaches include drug therapy, radio frequency ablation, and the implantable cardioverter defibrillator.

Calcium antagonists are the drugs of choice for treatment. These drugs regulate electrical conduction by blocking the calcium channels of myocardial cells.

Radio frequency ablation includes the placement of a catheter into the heart. High frequency radio waves are then introduced into the heart through the catheter to remove the faulty area through burning to neutralize faulty accessory electrically-conductive pathways.

One of the most common methods for treating arrhythmia is through electrical therapy delivered directed to the heart or through the body to the heart. Electrical currents or shocks are delivered to the heart to alter its rhythm. An implantable cardioverter defibrillator or ICD has electrodes which are connected to the heart.

The modern ICD is a small, battery powered device which stimulates the heart directly using function generators having specific waveforms to respond to and treat arrhythmias. The ICD and its electrode leads are implanted in the patient. The ICD monitors the activity of the heart and, when a determination is made that an irregularity such as ventricular fibrillation is occurring, the ICD delivers a relatively large defibrillation countershock to the electrodes implanted about the heart to return the heart to a prescribed heart rhythm rate. The defibrillation electrical countershock is typically in the range of between 25 and 40 joules. The countershock is relatively significant and is generated by high voltage capacitors which may be charged to between about 650 and 750 volts.

Installation of the ICD and its accompanying electrodes includes more than surgical insertion and attachment. Almost all known implantable ICD's may be configured or programmed to customize the functioning of the ICD to the particular needs of the patient. Each programmable ICD includes a set of parameters to respond to the needs of the individual patient in the most optimum way. Such parameters include fibrillation detection rate, high rate tachycardia detection rate, and rate cutoff for low rate ventricular tachycardia. The accuracy of the parameter settings for applying appropriate therapy are critical. For example, if the rate setting for defibrillation or cardioversion detection is too high, a fibrillating heart may be overlooked. If the setting for defibrillation or cardioversion detection is set too low, the ICD will incorrectly deliver an unnecessary countershock.

While automization of the programming of the ICD has been proposed (for example, the Sensolog [trademark; Siemens-Elema AB] pacemaker is alleged to be autoprogrammable), the typical ICD requires manual programming. Programmable pacemakers include, for example, the Activitrax II Models 8412-14 [trademark; Medtronic Inc.], the Legend Models 8416-18 [trademark; Medtronic Inc.], the Meta MV Model 1202 [trademark; Telectronics], the Sensor Model Kelvin 500 [trademark; Cook Pacemaker Corporation], the Prism CL Model 450A [trademark; Cordis Pacing System], and the Nova MR [trademark; Intermedics]. Each of these units requires at least some manual physician programming for parameters such as mode, sensitivity, threshold lower and upper rates, pulse amplitude, refractory period and pulse width.

While programmable features as well as procedures for programming the various pacemakers vary from one manufacturer to the next, each of the programmable ICD's requires that the programmer establish one or more baselines to provide the values necessary for programming the particular pacemaker to the particular needs of the afflicted individual. One method of obtaining a baseline is to have the patient undertake a certain minimum level of physical activity. However, the only accurate way to provide the necessary values to respond to the particular patient's arrhythmia is to induce the arrhythmia itself. Given in a controlled environment, this is of minimum risk to the patient. However, repetitious induction of the arrhythmia is usually required and, regardless of the safety of the environment, repeated inductions is not the preferred resolution.

Recognizing the shortcomings of known technologies, several approaches have been proposed in an effort to overcome difficulties in programming the ICD prior to implantation. Examples include: U.S. Pat. No. 5,226,413, issued Jul. 13, 1993, to Bennet et al. for "Rate Responsive Pacemaker And Method For Automatically Initializing The Same," which teaches a pacemaker system that includes a dual sensor implantable pacemaker and an external programmer for automatically and simultaneously optimizing and initializing a plurality of pacing parameters; U.S. Pat. No. 5,292,341, issued on Mar. 8, 1994, to Snell for "Method And System For Determining And Automatically Adjusting The Sensor Parameters Of A Rate-Responsive Pacemaker," which teaches a rate-responsive pacing system and method that allows the inter-related sensor operating parameters associated with the physiological sensor of a rate-responsive pacemaker to be automatically and/or optimally set for a particular patient; U.S. Pat. No. 5,421,830, issued Jun. 6, 1995, for Epstein et al. which teaches a programming system that allows a physician or medical personnel to optimize the settings of various arrhythmia detection criteria and/or parameters related to hemodynamic performance to be programmed into the implanted cardiac stimulating device; and U.S. Pat. No. 5,607,460, issued Mar. 4, 1997, to Kroll et al. for "Physician Interface Expert System For Programming Implantable Arrhythmia Treatment Devices," which teaches an interface expert system that allows a physician not well versed in ICD parameters to program at least one parameter into an ICD using the physician's existing knowledge of the patients medical history.

While each of these references provides a contribution to the art of the programming of parameters for pacemakers, a simple yet exacting method of programming remains wanting.

SUMMARY OF THE INVENTION

The present invention provides an in-vitro testing system to assist in optimal programming of an ICD which avoids the inconvenience and health risk associated with repetitive inductions of an arrhythmia. The system includes a high speed computer having analog-to-digital and digital-to-analog subsystems. The system includes software which provides real-time capture and storage of a patients electrogram. Subsequently, the electrogram may be played and replayed into ICD software simulators at a variety of settings to determine candidate programming parameters. The system further includes an attenuator through which signals are fed on their way to an ICD. This arrangement provides a method by which validation of the simulation system may be achieved. The system also provides for the capture of output event markers simultaneously with the signal into a digital file for assessment of device performance.

Other features and advantages of the present invention will become clearer according to the detailed description set forth below.

BRIEF DESCRIPTION OF THE DRAWING

The present invention will be more fully understood by reference to the following detailed description of the preferred embodiments of the present invention when read in conjunction with the accompanying drawing, in which the FIGURE is a diagrammatic representation of the system according to the present invention.

DETAILED DESCRIPTION OF THE PREFERRED EMBODIMENT

The drawing discloses the preferred system of the present invention. While the configuration of the system according to the illustrated diagram is preferred, it is envisioned that alternate system configurations of the present invention may be adopted without deviating from the invention as portrayed. The preferred embodiment is discussed hereafter.

The in-vitro ICD programming system is generally illustrated as 10. As anticipated for in-vitro, the system 10 is operably associated with a patient 12 to obtain an electrogram, although repeatable arrhythmic events could be provided for confirmation and testing by a mechanical means capable of generating a synthetic or test electrogram may be used as well as set forth below. The system 10 is operably associated with an ICD 14.

The system 10 includes an input amplifier 20, an input analog-to-digital (A/D) subsystem 22, a storage apparatus 24 for storing new incoming electrograms, a conduit 26 for directing the transmission of electrograms, a digital-to-analog (D/A) subsystem 28, and an output-to-ICD attenuator 30. The system 10 further includes an ICD-to-input attenuator 32, an output analog-to-digital subsystem 34, a recorder 36 for recording ICD behavior, and a display 38.

As is known and as is illustrated, the ICD 14 includes a pace sensor 40 and a shock output 42. The ICD 14 further includes a marker channel 44.

In general, the operative of the system 10 of the present invention is as follows. A cardiac rhythm signal (which may be induced) is transmitted from the heart of the patient 12 to the signal amplifier 20. The amplifier 20 produces an amplified analog signal which is converted to a digital form by the subsystem 22 for storage in the storage apparatus 24. The stored information is delivered via the conduct 26 as desired and is connected to an analog signal by the subsystem 28. The analog signal passes through the attenuator 30 and to the ICD 14 for response. (This same information may be provided to the recorder 36 via the converting subsystem 34.) The ICD 14 produces a shock which passes through the attenuator 32 and the converting subsystem 34 to the recorder 36. The recorded information is displayed on the display 38 for analysis. Once stored, the original signal from the heart may be played and replayed as necessary to allow for proper programming of the ICD 14.

A variety of combinations of hardware connections may be employed and may be menu selected. Input choices are simulator-generated rhythms, digitized signal files (available from Ann Arbor Electrogram Libraries [AAEL], Ann Arbor, Mich.), tape recorded signals, or output signals from actual pacemaker or ICD devices. Output choices are real time display (computer monitor with display of signals and marker channels), digital signal file (capture of signals, marker channel from the ICD programmer that contains device-detected intervals and zone classification, device response and invocation of therapy choice, etc., to a digital file), a tape recorder, a strip chart recorder, or an actual ICD or pacemaker device being tested. According to this arrangement, utilities to edit the AAEL digitized signal files are included, e.g., the operator can extract portions, concatenate sections to create combinations, strip out individual channels from multi-channel data, perform cursor-based interval measurements within a channel or across channels, and produce strip chart renditions or laser printouts.

The Electrogram Architect and Device Analyzer (EADA) is based on an Intel Pentium microprocessor with a speed of 133 Mhz and is supplemented with the high speed analog-to-digital (A/D) and digital-to-analog (D/A) subsystems (National Instruments) and a signal conditioning/voltage-protection subsystem. All sample and signal generation rates are 1 KHz (crystal controlled) except two test platform inputs from the device under test. These two data streams are sampled at 4 KHz for recognition of pacing stimulus and shock events. All A/D and D/A conversions are 12-bit calibrated to ±0.3 LSB (least significant bit) typical and ±1.0 LSB maximum, and provide between 10 to 100 times higher resolution than any of the available programmable devices. The signal conditioning/voltage-protection subsystems has a 1000:1 attenuator with variable fine tuning for conditioning 1 to 5 V signals for delivery to active devices, and a 4000:1 voltage divider to deliver an attenuated device response signal to the computer interface. All software contained within EADA for control of all system components (including commercial A/D and D/A boards) is specifically designed for application in the system of the present invention.

The system 10 of the present invention can provide standardized testing and evaluation of existing and future implantable cardioverter defibrillator pacemaker devices, i.e., active implants. The system 10 is designed to connect a variety of synthetic, real-time, or pre-recorded source signals to an ICD or pacemaker for purposes of evaluation of the response of the device under test in a variety of user controllable circumstances. The activity of the device is displayed and recorded in real-time as test protocols (described below) are presented to the device. Recorded events are analyzed in the immediate mode, captured for archival storage, and held for later statistical assessment.

System Verification

Four ventricular tachycardia (VT), three supraventricular tachycardia (SVT), three atrial flutter (Afl), three atrial fibrillation (Afb), and ten ventricular fibrillation (VF) passages were used to verify operation of the system 10. Test settings were 110/160 beats per minutes (bpm) for detection rate and five seconds for shock delay. The simulator and ICD detected the episodes for all passages at the 110 bpm setting. For the setting of 160 bpm, 2 VT's, 2 SVT's, 3 Afls, and 9 VF's were detected by the device, but no Afb triggered a shock. The simulator detection criteria were met by 2 VT's, 2 SVT's, 3 Afls, 10 VF's, and 1 Afb. The mean detection time was 6869/7330 ms (110 bpm/160 bpm) for the simulator and 7840/8170 ms for the device. A comparison of the results showed general agreement between the simulator and the device. The results demonstrated that behavior of the device at a variety of settings can be elucidated by the simulator for selection of optimal performance. It was also determined that the automated system can also function as test-bed evaluation of new algorithms during device development and design.

Test Protocols

Test protocols were established by defining a series of one or more configurations (arrhythmic events), each for a predetermined period of time. Each configuration defines signal sources, signal destinations, and choice of output to an ICD or pacemaker simulator. Any number of configurations may be included within a given protocol. For example, the first configurations may be included within a given protocol. For example, the first configuration of a test protocol could couple real-time synthetic sinus rhythm signals to an ICD simulator and deliver the device response to the real-time display, to a computer digital signal file, to an analog or digital tape recorder, and a strip chart recorder all simultaneously and in real-time. The configuration might, after a programmed period of time, switch from sinus rhythm to ventricular tachycardia and hold this mode until operator intervention or completion of the programmed protocol duration specified for this configuration. Any number of sequences as complex or as simple as desired may be easily defined within a protocol.

Clinical Data

Multiple electrogram passage recordings were obtained for clinical analysis. Applicable recordings are available from Ann Arbor Electrogram Libraries, Ann Arbor, Mich. For example, Volume I of the recordings has been licensed by 11 pacemaker companies and is being used for development purposes in the design of next-generation ICD's. Volume I contains multiple recordings from 63 patients, including a baseline sinus rhythm passage, or more arrhythmia passages, and a section containing calibration pulses. The date have wideband filter settings (1–500 Hz), gains are held constant throughout the recordings, and digital versions in CD-ROM format are digitized at 1000 Hz. Volume II contains 52 additional patient recordings in a similar format. Volume III contains restricted patient data which is available as a test set for assessing sensitivity and specificity of ICD detection algorithms in an independent setting. Volume IV contains the recordings of 16 patients with atrial fibrillation, sometimes with competing ventricular arrhythmias. Volume V contains recordings of patients with atrial fibrillation or AV re-entrant tachycardia. (Atrial fibrillation is cited repeatedly in literature as the most frequent cause of false shocks, ranging from 10–74%.)

The collection of data was executed under a carefully prescribed recording protocol which ensures constancy of electrode placement and gain settings. The database contains surface leads (2 or 3), unipolar high right atrial (HRA) lead, a bipolar HRA lead, a unipolar right ventricular apex (RVA) lead, and a bipolar RVA lead. The data is particularly valuable because of its inclusion of atrial electrograms which are notably absent from other collections. A newly released ICD (the ELA "Defender") has two-channel sensing and pacing capabilities. Other manufacturers are expected to introduce their own versions of two-channel devices.

Experimental Testing of Commercially Implemented Algorithms

Four computer programs were designed in order to demonstrate the feasibility of the system 10 of the present invention for evaluation of ICDs. The programs precisely emulate algorithms used by three recently introduced third-generation ICDs (PCD Jewel, Medtronic, Inc.; Cadence, Ventritex, Inc.; Ventak PRx, CPI) and one second-generation ICD (Ventak P2, CPI). In each case, the tachycardia detection algorithm described in the Physician's Manual was flow-charted and programmed for emulation of expected device performance. A set of tape recordings made during provocative electrophysiology studies (undertaken by the University of Chicago) was digitized at 1000 Hz; 130 30-second records of normal and abnormal rhythms were produced by personnel not familiar with the algorithms to be tested. The ventricular intervals in these records were measured by a previously published sensing program (R.

MacDonald, J. Jenkins, R. Arzbaecher, R. Throne, *A Software Trigger for Intracardiac Waveform Detection with Automatic Threshold Adjustment*, Comp. Cardiol., pp. 167–170, 1990) which contains the same automatic thresholding scheme used in the PCD and functionally resembles the automatic gain control used by Cadence and Ventak PRx. These 130 VV interval records formed the test data for evaluating the performance of the four tachycardia detection algorithms. The test data include: 33 sinus rhythms (RS), 7 atrial tachycardias (AT), 12 atrial fibrillations (AF), 9 atrial flutters (AFL), 16 atrioventricular reentrant tachycardias (AVRT), 35 ventricular tachycardias (VT), and 18 ventricular fibrillations (VF).

Algorithm Testing

Four C-language programs were written which implement the tachycardia detection algorithms in each of the four devices. The VV interval sequence from 130 digitized arrhythmia records was processed in exactly the same way that the microprocessor would process the information.

Results

Typical physician-selected zone ranges were programmed for 12 combinations to assess sensitivity and specificity of diagnosis in 130 rhythm passages. Detection intervals were chosen as combinations of the following parameters: 360 and 450 ms for slow VT; 260, 340, and 400 ms for fast VT; and incrementally from 280 to 320 ms for VF. Agreement of ICD with physician diagnosis ranged from 71% to 79% depending on device and/or settings. Sensitivity of ICD diagnosis for VF was 100% and specificity was 80% to 86% depending on device and choice of setting. Misdiagnoses of VT as VF represented 77% to 89% of VF errors, while supraventricular rhythms (SVRs) constituted 11% to 23% of VF errors. Sensitivity of VT diagnosis (given that VT was recognized as either VT or VF, i.e., therapy was delivered) ranged from 71% to 97% across all three device simulations. VT specificity was 75% to 94%. Distribution of SVRs misdiagnosed as VT/VF, respectively, was on average 1.1/0 AF, 2.0/0 AFL, 0.5/0 AT, 11.4/3.4 AVRT, and 1.5/0 SR patients. There were no significant misclassification differences between devices. This computer simulation of third-generation ICD detection algorithms afforded a systematic study of a variety of commonly used settings which expose hazards of misdiagnosis and mistaken choice of therapy. False therapy based on misclassification of VT as VF was the greatest source of error, supplanting the high incidence of SVRs which were the major cause of error in second-generation ICDs. Statistics related to this study are highly dependent on the mix of arrhythmias present in the database, but demonstrate the possibility of a comprehensive examination of device settings for assessment of efficacy for the arrhythmia being treated.

These simulators of third-generation ICDs represent an important component of the testing device by demonstrating that the technology exists to provide robust independent testing of any new algorithmic modifications to medical devices which employ diagnostic software.

Actual ICD Device Testing

Ten ICDs, explanted from patients during a replacement implant, have been evaluated by the system of the present invention. All 10 had recorded histories of shock therapy delivery (41±33) prior to being acquired. Devices were CPI Models P (n=9) and P2 (n=1). Six ICDs were tested with a variety of detection settings (8 of 10 beats exceeding the fibrillation rate which ranged from 110 bpm to 220 bpm) combined with a 5 s sustained period of subsequent detection. Arrhythmia passages from AAEL Volume 1 and II (discussed above) were chosen at rates necessary to demonstrate both rate compliance (followed by shock) and rate noncompliance (no shock). First-shock energy level was set to Joules (programmable) followed by 4 additional shocks at 34 Joules (non-programmable). Arrhythmia passages were of lengths appropriate to assess the redetection capabilities for delivery of repeated shocks. One ICD (Model P2) with two detection zones (VT and VF) was evaluated at 5 distinct settings until battery depletion.

A second stage of tests was performed on 3 ICDs (Model P) in which three arrhythmia passages were delivered for two fibrillation zone settings (110 bpm and 160 bpm) within each device. Shock levels were set to 2 Joules to conserve batteries and test episodes of arrhythmias were reduced to 15 s in length to suppress subsequent redetections eliciting additional 34 Joule shocks. This was done in order to ensure 6 complete tests within each ICD. In all cases, detection or non-detection behavior was in agreement with manufacturer specifications and simulation predictions. Time for capacitor charge before shock delivery ranged from 4.3 s to 20.0 s depending on order of shocks, energy level of shocks, and time to battery end-of-life.

In the second stage of this initial testing, device response was captured on-line by the EADA system into a 3-channel signal file containing (Ch1) the digitized RVA signal being delivered to the device, (Ch2) attenuated recording of the output shock of the ICD, and (Ch3) the marker channel of the ICD programmer (CPI Model 2035). The programmer marker signal displays pulses of varying amplitude which indicate initial detection (8/10 beats exceeding the rate selected), continuing detection for 5 s, beginning and end of charge period, and shock delivery. The ventricular signal and marker channel were simultaneously recorded on a 2-channel strip chart recorder for off-line measurement and validation. This initial testing protocol demonstrated the functional capability of the EADA system to provide output signals in attenuated form, and to capture the device response with associated markers into a digital test-history file.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

What is claimed is:

1. An in-vitro testing system to assist in the optimal programming of a cardiac pacemaker for use in conjunction with a heart, the system including:

an input amplifier;

an input analog-to-digital subsystem connected to said input amplifier;

a storage apparatus for storing new incoming electrograms of a patient, said electrograms being defined by a series of digitized wave forms selected from the group consisting of normal and abnormal rhythms, said storage apparatus being connected to said analog-to-digital subsystem, said storage apparatus including system hardware for responding to system software, said storage apparatus further including system software for providing real-time capture and storage of said incoming electrograms;

a digital-to-analog subsystem connected to said storage apparatus;

an output-to-ICD attenuator connected to said digital-to-analog subsystem;

a programmable cardiac pacemaker connected to said output-to-ICD attenuator;

an analyzer for evaluating the response of said programmable cardiac pacemaker; and leads for providing operative connection with the heart.

2. The in-vitro testing system of claim 1, said system further including an ICD-to-input attenuator connected to said programmable cardiac pacemaker.

3. The in-vitro testing system of claim 2, said system further including an output analog-to digital subsystem connected to said ICD-to-input attenuator.

4. The in-vitro testing system of claim 3, said system further including a recorder for recording ICD behavior connected to said output analog-to digital subsystem.

5. The in-vitro testing system of claim 4, said system further including a display connected to said recorder for recording ICD behavior.

* * * * *